United States Patent [19]

Matsushita et al.

[11] Patent Number: 4,841,075

[45] Date of Patent: Jun. 20, 1989

[54] METHOD OF PREPARING ACETAL OR KETAL

[75] Inventors: Hajime Matsushita, Yokohama; Makoto Shibagaki, Kawasaki; Kyoko Takahashi, Tokyo; Hideyuki Kuno, Yokohama, all of Japan

[73] Assignee: Japan Tobacco, Inc., Tokyo, Japan

[21] Appl. No.: 129,702

[22] Filed: Dec. 7, 1987

[30] Foreign Application Priority Data

Dec. 11, 1986 [JP] Japan ................................. 61-293470

[51] Int. Cl.$^4$ ................... C07D 317/00; C07D 317/22
[52] U.S. Cl. .................................... 549/341; 549/336; 549/337; 549/429; 568/591; 568/594
[58] Field of Search ............... 549/429, 337, 336, 341; 568/591, 594

[56] References Cited

U.S. PATENT DOCUMENTS

| | | | |
|---|---|---|---|
| 3,056,817 | 10/1962 | Werber et al. | 549/341 |
| 3,725,438 | 4/1973 | Barone et al. | 549/341 |
| 3,769,303 | 10/1973 | Easter et al. | 549/341 |
| 4,173,570 | 11/1979 | Cleare | 549/341 |
| 4,289,700 | 9/1979 | Yoshida et al. | 549/341 |
| 4,518,785 | 5/1985 | Eckhardt et al. | 568/594 |
| 4,579,980 | 4/1986 | Kogoma et al. | 568/594 |

*Primary Examiner*—Asok Pal
*Attorney, Agent, or Firm*—Nixon & Vanderhye

[57] ABSTRACT

A method of preparing an acetal or ketal from a corresponding aldehyde or ketone is disclosed. A hydrous oxide of an element of Group IV of the Periodic Table is used as a catalyst, and the aldehyde or ketone is caused to react with an alcohol. The hydrous oxide can be obtained by partially dehydrating a hydroxide of the corresponding element. The method does not require an acid catalyst and is applicable to a carbonyl compound which is not stable in acids.

5 Claims, No Drawings

METHOD OF PREPARING ACETAL OR KETAL

BACKGROUND OF THE INVENTION

1. Field of the Invention

The present invention relates to a method of preparing an acetal or a ketal and, more particularly, to a method of preparing an acetal or ketal by causing an aldehyde or ketone to react with an alcohol in the presence of a catalyst.

2. Description of the Prior Art

When used in a variety of reactions, an acetal group or a ketal group is less reactive than a carbonyl group and can be easily converted into a carbonyl group. For this reason, when an aldehyde or a ketone is to be used in a desired reaction, it is first converted into an acetal or ketal. After the reaction has taken place, the reaction product is then converted into an aldehyde or ketone. That is to say, the acetal or ketal is very important as a protection group of the carbonyl group. An acetal or ketal is also important as a source material for synthetic perfume.

An acetal or ketal can be obtained by any one of the following reactions: acetylene reacting with an alcohol, an organometallic compound with an orthoester, vinyl ether with an alcohol, or a gem-dihalide with a metal alcoholate.

A more popular method of preparing an acetal or ketal is one in which an aldehyde or a ketone is used as a starting material and converted into a corresponding acetal or ketal. This method employs a synthesis reaction, for example, in which an aldehyde or ketone is made to react with an orthoester. However, the orthoester is expensive and is not easily available.

Therefore, another synthesis reaction is more often employed, in which an aldehyde or ketone is allowed to react with an alcohol. This synthesis reaction is performed in a solvent such as benzene in the presence of an acid catalyst. Water, which occurs as a by product, is removed by azeotropic distillation. Typical acid catalyst is a mineral acid (e.g., sulfuric acid or a p-toluenesulfonic acid) or its derivative, although in recent years, an organic acid which is soluble in organic solvents has also come into use for the same purpose. Use of this method, however, presents the following problems:

First, since the synthetic reaction takes place in a homogeneous solution, a number of complicated operations must be performed, following the reaction, in order to isolate the product thereof. In particular, since the acid used as a catalyst is strong, a large quantity of alkaline water must be used to neutralize the solution, in order to separate the catalyst. Thus, a cooling operation is required, in order to eliminate the heat produced in the neutralizing process, and also a liquid separation operation.

Second, since a strong acid catalyst is used, the reaction vessel tends to become corroded, and the heating required in this reaction merely accelerates the corrosion process.

Third, since a strong acid is used as the catalyst, an aldehyde or ketone (e.g., 4-hydroxy-2-butanone) which is not stable in acidic conditions cannot be used as a starting material.

SUMMARY OF THE INVENTION

It is an object of the present invention to provide a low-cost method of preparing an acetal or a ketal, wherein an aldehyde or ketone can be made to react sufficiently with an alcohol in neutral conditions, and the product thereof can be isolated without the need for complicated treatment operations after the reaction is completed.

According to the present invention, there is provided a method of preparing an acetal or ketal, which comprises causing an aldehyde or ketone to react with an alcohol by using as a catalyst a hydrous oxide of an element of Group IV of the Periodic Table, thereby obtaining an acetal or ketal corresponding to the aldehyde or ketone.

The hydrous oxide used as the catalyst in the present invention is a rigid, solid material which is physically and chemically stable, and is obtained by partially dehydrating the hydroxide of the corresponding element. It is insoluble in water, alcohols, or any other organic solvents, as well as being chemically and thermally stable and inexpensive to produce. It is also highly active as a catalyst for accelerating a reaction between an aldehyde or ketone and an alcohol.

DETAILED DESCRIPTION OF THE PREFERRED EMBODIMENT

The most important characteristic feature of the present invention is the use, as a catalyst, of a hydrous oxide of an element of Group IV of the Periodic Table, zirconium hydrous oxide, titanium hydrous oxide, or tin hydrous oxide being the most preferable. The hydrous oxide of the selected element can be obtained as follows:

A hydroxide of the element is heat-treated under the conditions which do not allow dehydration of the hydroxide into a pefect oxide, so that the hydroxide is partially dehydrated. For example, when zirconium hydroxide is heated at a temperature of 500° C. or more at atmospheric pressure, it is completely dehydrated to obtain zirconia ($ZrO_2$). However, when zirconium hydroxide is heated at about 300° C., zirconium hydroxide is partially hydrated to obtain a stable state. During the heat treatment, the weight of zirconium hydroxide is reduced by about 17% in about an hour, but subsequent weight loss rarely occurs. The same operations as described above can be performed for hydroxides of other elements other than zirconium.

The hydrous oxide is a rigid, white, solid material. Since it is also amorphous, it cannot be analyzed by X-ray diffraction, and thus its detailed chemical structure is not known. However, the chemical structure of the hydrous oxide can be assumed on the basis of the fact that the hydroxide is partially dehydrated. The hydrous oxide has an Elm-O-Elm bond (Elm represents an element of Group IV of the Periodic Table) formed by dehydration-condensation, and hydroxyl groups directly bonded to Elm atom are also present. As described above, the hydrous oxide is insoluble in water and organic solvents and is stable as a heterogeneous catalyst. The hydrous oxide does not cause problems such as elution and swelling and is excellent in heat resistance and solvent resistance. The hydrous oxide can be repeatedly used due to the above properties. In addition, the hydrous oxide is confirmed to have low surface acidity and good ion exchangeability with various ions.

The hydrous oxide can be easily obtained at low cost as follows. A hydroxide is obtained from minerals buried in a relatively large amount and is heat-treated and partially dehydratd to obtain the hydrous oxide. When this hydrous oxide is used as a catalyst, it may be pulverized into grains having a proper size or may be supported on a proper carrier such as alumina, active charcoal, silica gel, silica-alumina, or zeolite.

The present invention can be properly embodied as follows.

The above catalyst, an aldehyde or ketone and an alcohol are mixed in a suitable vessel. The content of the aldehyde or ketone is 0.1 to 100 mmol and more preferably 1 to 10 mmol with respect to 1 g of the catalyst. The alcohol content is 0.4 to 1,000 mmol and more preferably 1 to 40 mmol with respect to 1 g of the catalyst. The volume of the solution is 5 to 100 ml and preferably 7 to 20 ml with respect to 1 g of the catalyst. If required, the solution can be diluted by an organic solvent (e.g., benzene or toluene) which does not react with the catalyst. The reaction solution is heated at a temperature falling within the range of room temperature to the boiling temperature of the solvent and is allowed to chemically react for a predetermined period of time. The optimal reaction time varies with the reaction temperature. After the reaction, the catalyst is removed by filtration. When the filtered solution is distilled, an acetal or ketal corresponding to the aldehyde or ketone as the starting material can be obtained.

Preparation of the catalyst used in the present invention, and preparation of an acetal or ketal according to the present invention will now be described in detail, by way of examples.

EXAMPLE 1

(Preparation of Catalyst)

In this example, 200 g of zirconium oxychloride (octahydrate) were dissolved in 10 l of deionized water, and a 1N sodium hydroxide aqueous solution was gradually added under stirring thereto to attain a pH of 6.80, as a result of which a hydrated gel of zirconium hydroxide was obtained. The resultant hydrated gel was filtered, and was washed with fresh deionized water. Washing continued until no chloride ions were detected in the filtrate. The resultant hydrated gel was dried and cut into pieces, and the pieces placed on a glass plate, and then dried. When the dried pieces were placed in deionized water, they rapidly broke up into grains of various sizes. The grains were filtered and separated from the water, and were dried in an enameled butt at room temperature, whereby 90 g of pulverized zirconium hydroxide were obtained.

Zirconium hydroxide grains having 24 to 60 mesh sizes were recovered and heated at 300° C. and atmospheric pressure for 3 hours, and were partially dehydrated, whereby zirconium hydrous oxide was obtained. The weight loss due to heating was approximately 17%.

EXAMPLE 2

(Preparation of Catalyst)

In this example, 10 l of deionized water were poured in a vessel, and 190 g of titanium tetrachloride were dissolved in the water under stirring. 28% aqueous ammonia solution was gradually added to control the pH value to 7. A hydrated gel of titanium hydroxide was precipitated and, the resultant hydrated gel was filtered through a Buchner funnel and then washed with deionized water until no chloride ions were detected in the filtrate. The resultant hydrated gel was cut into pieces by a knife, so as for the gel to dry more quickly. The pieces were then placed on a glass plate and dried at room temperature. When the dried pieces were placed in deionized water, they quickly broke up into grains of various sizes. The grains were filtered and dried in an enameled butt at room temperature, whereby 30 g of pulverized titanium hydroxide were obtained.

Titanium hydroxide grains having 24 to 60 mesh sizes were recovered and heated at 300° C. and atmospheric pressure for 3 hours and were partially dehydrated, whereby titanium hydrous oxide was obtained.

EXAMPLE 3

(Preparation of Catalyst)

261 g of tin tetrachloride were added dripwise to 4 l of deionized water and 28% aqueous ammonia solution was gradually added thereto under stirring, to control a pH to 7, thereby precipitating a hydrated gel of tin hydroxide. The resultant hydrated gel was filtered through a Buchner funnel and was washed with deionized water until no chloride ions were detected in the filtrate. The resultant hydrated gel was cut into pieces by a knife, so as for the gel to dry more quickly. The pieces were placed on a glass plate and were dried at room temperature. When the dried pieces were placed in deionized water, they quickly broke up into grains of various sizes. The grains were filtered and dried in an enameled butt at room temperature, as a result of which 141 g of transparent, pulverized tin hydroxide were obtained.

Tin hydroxide grains having 24 to 60 mesh sizes were recovered and heated at 300° C. and atmospheric pressure for 5 hours and were partially dehydrated, whereby tin hydrous oxide was obtained.

EXAMPLE 4

(Preparation of Acetal by Ethylene Glycol)

0.5 g (0.5 mmol) of n-hexanal and 0.62 g (10 mmol) of ethylene glycol were dissolved in 10 ml of benzene in a 25-ml eggplant type flask. 1.0 g of the zirconium hydrous oxide prepared in Example 1 was added to the mixture. The resultant solution was heated by a mantle heater and slowly refluxed. After the solution had reacted for 4 hours, it was cooled and filtered to eliminate the catalyst. The solvent was then evaporated and subjected to reduced pressure distillation, whereby 0.71 g of n-hexanal ethyleneglycoxy acetal were obtained (yield: 98%).

EXAMPLE 5

(Preparation of Acetal and Ketal by Ethylene Glycol)

Acetals or ketals corresponding to various carbonyl compounds were prepared following the same procedures as in Example 4, except that the various carbonyl compounds and the ethylene glycol shown in Table 1 were used as starting materials.

In all the reactions, 1.0 g of the zirconium hydrous oxide as a catalyst, 5 mmol of each carbonyl compound, and 10 ml of the solvent were used. The reaction conditions were selected from among A, B, and C.

A: reflux in a benzene for 4 hours
  B: reaction in tetrahydrafurane at room temperature for 20 hours
  C: reaction in benzene with azeotropic dehydration for one hour The products were analyzed by gas chromatography. The results of the analysis are summarized in Table 1.

TABLE 1

| CARBONYL COMPOUND | PRODUCT ACETAL OR KETAL | CARBONYL:ETHYLENE GLYCOL | REACTION CONDITION | YIELD (%) |
|---|---|---|---|---|
| pentanal (CH₃(CH₂)₃CHO) | 2-butyl-1,3-dioxolane | 1:1 | A | 90 |
| " | " | 1:2 | B | 65 |
| octanal (CH₃(CH₂)₆CHO) | 2-heptyl-1,3-dioxolane | 1:2 | A | 92 |
| cyclohexanecarbaldehyde | 2-cyclohexyl-1,3-dioxolane | 1:2 | A | 98 |
| benzaldehyde | 2-phenyl-1,3-dioxolane | 1:2 | A | 72 |
| benzaldehyde | 2-phenyl-1,3-dioxolane | 1:2 | C | 80 |
| 2-phenylbutanal | 2-(1-phenylpropyl)-1,3-dioxolane | 1:2 | A | 80 |
| cyclohexanone | 1,4-dioxaspiro[4.5]decane | 1:1 | A | 74 |
| " | " | 1:2 | A | 90 |
| " | " | 1:2 | B | 72 |
| " | " | 1:1 | C | 83 |
| 2-methylcyclohexanone | ketal | 1:2 | B | 31 |
| 4-methylcyclohexanone | ketal | 1:2 | B | 79 |
| 2-nonanone | 2-methyl-2-heptyl-1,3-dioxolane | 1:1 | A | 32 |
| 5-chloro-2-pentanone | 2-methyl-2-(3-chloropropyl)-1,3-dioxolane | 1:1 | A | 80 |

TABLE 1-continued

| CARBONYL COMPOUND | PRODUCT ACETAL OR KETAL | CARBONYL:ETHYLENE GLYCOL | REACTION CONDITION | YIELD (%) |
|---|---|---|---|---|
| PhC(O)CH₃ | Ph-C(CH₃)(OCH₂CH₂O) | 1:2 | A | 30 |
| (CH₃)₂C=CHC(O)CH₃ | corresponding ketal | 1:2 | A | 15 |
| CH₃C(O)CH₂CH₂OH | corresponding ketal with OH | 1:2 | B | 28 |

EXAMPLE 6

(Preparation of Acetal by Methanol or Ethanol)

10 ml of methanol or ethanol were added to 0.5 g (0.5 mmol) of n-hexanal in a 25-ml eggplant type flask. 1.0 g of zirconium hydrous oxide prepared in Example 1 was added to the mixture. The resultant solution was heated by a mantle heater and slowly refluxed for 4 hours.

The reaction products were analyzed by gas chromatography, and the following result was obtained:

The reaction product obtained by using methanol was n-hexanal dimethylacetal (yield: 100%), and that obtained by using ethanol was n-hexanal diethylacetal (yield: 91%).

EXAMPLE 7

(Preparation of Acetal or Ketal by Various Catalysts)

Acetals were prepared in the same procedure as in Example 1, by using n-hexanal and ethylene glycol and various catalysts. Ketals were prepared using cyclohexanone and ethylene glycol. The results of product analysis are summarized in Table 2.

The titanium hydrous oxide and tin hydrous oxide used as the catalysts were as prepared in Examples 2 and 3, respectively. Commercially available active alumina and silica for chromatography were used as comparative catalysts.

TABLE 2

| CARBONYL COMPOUND | PRODUCT ACETAL OR KETAL | CATALYST | YIELD (%) |
|---|---|---|---|
| n-hexanal (CHO) | cyclic acetal | TITANIUM HYDROUS OXIDE | 83 |
| cyclohexanone | cyclic ketal | " | 87 |
| n-hexanal (CHO) | cyclic acetal | TIN HYDROUS OXIDE | 34 |
| cyclohexanone | cyclic ketal | " | 39 |
| n-hexanal (CHO) | — | ACTIVE ALUMINA | 0 |
| cyclohexanone | — | " | 0 |

TABLE 2-continued

| CARBONYL COMPOUND | PRODUCT ACETAL OR KETAL | CATALYST | YIELD (%) |
| --- | --- | --- | --- |
|  | — | SILICA FOR CHROMATOGRAPHY | 0 |
|  | — | SILICA FOR CHROMATOGRAPHY | 0 |

According to the method of the present invention as described above, the acid catalyst need not be used, and the acetal or ketal can be prepared from a carbonyl compound (e.g., 4-hydroxybutanone) which is unstable in acids. Various other advantages can be provided by the invention. For example, the catalyst can be used repeatedly.

What is claimed is:

1. A method of preparing an acetal or ketal, which comprises causing an aldehyde or ketone to react with an alcohol by using a hydrous oxide of an element of Group IV of the Periodic Table as a catalyst, whereby the acetal or ketal corresponding to the aldehyde or ketone is obtained.

2. A method according to claim 1, wherein the catalyst is one selected from the group consisting of a zirconium hydrous oxide, a titanium hydrous oxide, and a tin hydrous oxide.

3. A method according to claim 1, wherein the hydrous oxide pulverized into grains having a desired size is used without further modifications.

4. A method according to claim 1, wherein the hydrous oxide is carried on a suitable carrier selected from the group consisting of alumina, active charcoal, silica gel, silica-alumina, and zeolite.

5. A method according to claim 1, wherein the catalyst is used repeatedly.

* * * * *